United States Patent
Omiya et al.

(10) Patent No.: US 9,126,895 B2
(45) Date of Patent: Sep. 8, 2015

(54) REAGENT FOR MEASURING DEGREE OF OXIDATIVE STRESS AND METHOD OF MEASURING DEGREE OF OXIDATIVE STRESS

(71) Applicant: ARKRAY, Inc., Kyoto (JP)

(72) Inventors: Kazuhiro Omiya, Kyoto (JP); Toshihiro Imai, Kyoto (JP); Emi Ashibe, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/138,076

(22) Filed: Dec. 22, 2013

(65) Prior Publication Data
US 2014/0179016 A1    Jun. 26, 2014

(30) Foreign Application Priority Data

Dec. 25, 2012  (JP) ................................. 2012-281271
Dec. 2, 2013   (JP) ................................. 2013-249380

(51) Int. Cl.
| G01N 33/50 | (2006.01) |
| G01N 33/48 | (2006.01) |
| G01N 33/00 | (2006.01) |
| C07C 215/68 | (2006.01) |
| C07C 211/55 | (2006.01) |
| C07C 211/54 | (2006.01) |
| G01N 33/84 | (2006.01) |

(52) U.S. Cl.
CPC ............ C07C 215/68 (2013.01); C07C 211/55 (2013.01); G01N 33/84 (2013.01); *G01N 2800/7009* (2013.01); *Y10T 436/10* (2015.01); *Y10T 436/206664* (2015.01)

(58) Field of Classification Search
CPC ....... G01N 33/50; G01N 33/48; G01N 33/00; C07C 215/68; C07C 215/00; C07C 211/55; C07C 211/54; Y10T 436/00; Y10T 436/10; Y10T 436/206664; Y10T 436/20
USPC ................... 436/135, 127; 564/443, 434, 305
See application file for complete search history.

(56) References Cited

U.S. PATENT DOCUMENTS 5,912,179 A * 6/1999 Alvarez et al. .................. 436/63
2009/0246815 A1 * 10/2009 Shuto et al. ..................... 435/23

FOREIGN PATENT DOCUMENTS

| EP | 0783692 B1 | 11/1998 |
| EP | 2107122 A1 | 10/2009 |
| IT | 0001339727 B1 | 5/2007 |
| JP | 2009-257909 A | 11/2009 |
| JP | 2013-249830 * 12/2013 ............. G01N 33/50 |
| WO | 1996/09540 A1 | 3/1996 |

OTHER PUBLICATIONS

Alberti et al., "The Radical Cation of N,N-Diethyl-para-Phenylendiamine: a Possible Indicator of Oxidative Stress in Biological Samples," Research on Chemical Intermediates, 26: 253-267 (2000).
Takashima et al., "Assessment of antioxidant capacity for scavenging free radicals in vitro: a rational basis and practical application," Free Radical Biology & Medicine, 52: 1242-1252 (2012).
Extended European Search Report issued in counterpart European Patent Application No. 13198862.8 dated Feb. 24, 2014.

* cited by examiner

Primary Examiner — Christine T Mui
(74) Attorney, Agent, or Firm — Morgan, Lewis & Bockius LLP

(57) ABSTRACT

The present invention provides a reagent for measuring a degree of oxidative stress that includes a compound represented by the following general formula (I) or a salt thereof, and a method of measuring a degree of oxidative stress using the reagent for measuring a degree of oxidative stress. In the general formula (I), $R^1$, $R^2$, $R^3$ and $R^4$ each independently represent a hydrogen atom, an ethyl group, an isopropyl group, a hydroxyalkyl group that has 1 to 4 carbon atoms, or a phenyl group, and at least one of $R^1$, $R^2$, $R^3$ or $R^4$ represents an isopropyl group, a hydroxyalkyl group having 1 to 4 carbon atoms, or a phenyl group.

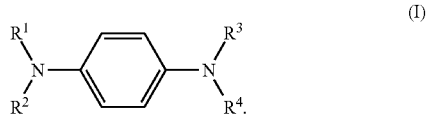

12 Claims, 2 Drawing Sheets

REAGENT FOR MEASURING DEGREE OF OXIDATIVE STRESS AND METHOD OF MEASURING DEGREE OF OXIDATIVE STRESS

CROSS-REFERENCE TO RELATED APPLICATION

The present application claims priority under 35 USC 119 from Japanese Patent Application No. 2012-281271 filed on Dec. 25, 2012, and Japanese Patent Application No. 2013-249380 filed on Dec. 2, 2013. The contents of that application are incorporated herein by reference in their entirety. All publications, patent applications, and technical standards mentioned in this specification are herein incorporated by reference to the same extent as if each individual publication, patent application, or technical standard was specifically and individually indicated to be incorporated by reference.

BACKGROUND

1. Technical Field

The present invention relates to a reagent for measuring a degree of oxidative stress and a method of measuring a degree of oxidative stress.

2. Background Art

It has been known that oxidative stress in vivo relates to various kinds of diseases or aging, and a variety of methods were proposed in order to understand the condition of oxidative stress in vivo. For example, it has been proposed that free radicals in a biological sample such as blood are used as a marker of oxidative stress.

Japanese Patent Application Laid-Open (JP-A) No. 2009-257909 discloses an analysis device analyzing the condition of free radicals in blood that is collected from a subject by measuring a degree of oxidative stress of a subject. In the analysis device, as one of the methods of measuring a degree of oxidative stress, a hydroperoxide (ROOH) in blood generated in vivo is used as a marker of oxidative stress, and the d-ROMs test (Reactive Oxygen Metabolites) has been applied in which the concentration of the hydroperoxide is measured by the color reaction. JP-A No. 2009-257909 discloses N,N-ethyl-p-phenylenediamine as a color reagent used when the d-ROMs test is performed.

In addition, European Patent (EP) No. 0783692B1 discloses that N,N-ethyl-p-phenylenediamine and a compound that has —$CH_3$, —$CH_2CH_3$, —H or a halogen atom as a coordinate functional group of four places thereof are used as a color reagent, and a method of measuring free radicals using the color reagent.

SUMMARY OF INVENTION

Technical Problem

However, in N,N-ethyl-p-phenylenediamine, or the like which is disclosed in JP-A No. 2009-257909 and EP No. 0783692B1, the absorption characteristics are insufficient, from either of viewpoints of sensitivity or the measuring wavelength range. The present invention has been made in the light of the circumstances described above and can provide a reagent for measuring a degree of oxidative stress capable of measuring a degree of oxidative stress with higher sensitivity or in a wider wavelength range than heretofore, and a method of measuring a degree of oxidative stress using the reagent for measuring a degree of oxidative stress.

Solution to Problem

The present invention is as follows.

<1> A reagent for measuring a degree of oxidative stress that includes a compound represented by the following general formula (I) or a salt thereof

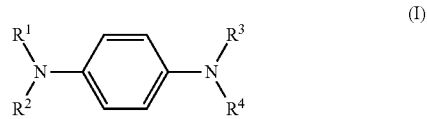

(I)

In the general formula (I), $R^1$, $R^2$, $R^3$ and $R^4$ each independently represent a hydrogen atom, an ethyl group, an isopropyl group, a hydroxyalkyl group having 1 to 4 carbon atoms or a phenyl group, and at least one of $R^1$, $R^2$, $R^3$ or $R^4$ represents an isopropyl group, a hydroxyalkyl group having 1 to 4 carbon atoms or a phenyl group.

<2> The reagent for measuring a degree of oxidative stress according to <1> in which at least one of the $R^1$, $R^2$, $R^3$ or $R^4$ is a hydroxyalkyl group having 1 to 4 carbon atoms.

<3> The reagent for measuring a degree of oxidative stress according to <1> in which at least one of the $R^1$, $R^2$, $R^3$ or $R^4$ is a 2-hydroxy ethyl group.

<4> The reagent for measuring a degree of oxidative stress according to <1> in which at least one of the $R^1$, $R^2$, $R^3$ or $R^4$ is a phenyl group.

<5> A method of measuring a degree of oxidative stress that includes measuring a degree of oxidative stress in a biological sample using the reagent for measuring a degree of oxidative stress according to any one of <1> to <4>.

<6> A compound represented by the general formula (I) or a salt thereof for manufacturing the reagent for measuring a degree of oxidative stress according to any one of <1> to <4>.

<7> A method of manufacturing the reagent for measuring a degree of oxidative stress according to any one of <1> to <4>, the method includes mixing the compound represented by the general formula (I) or the salt thereof and a buffer solution.

<8> A use of the compound represented by the general formula (I) or the salt thereof in manufacturing the reagent for measuring a degree of oxidative stress according to any one of <1> to <4>.

<9> A use of the reagent for measuring a degree of oxidative stress according to any one of <1> to <4> in the method of measuring a degree of oxidative stress.

Advantageous Effect of Invention

According to the present invention, a reagent for measuring a degree of oxidative stress capable of measuring a degree of oxidative stress with higher sensitivity or in a wider wavelength range than heretofore, and a method of measuring a degree of oxidative stress using the reagent for measuring a degree of oxidative stress can be provided.

DESCRIPTION OF EMBODIMENT

Figure 1:
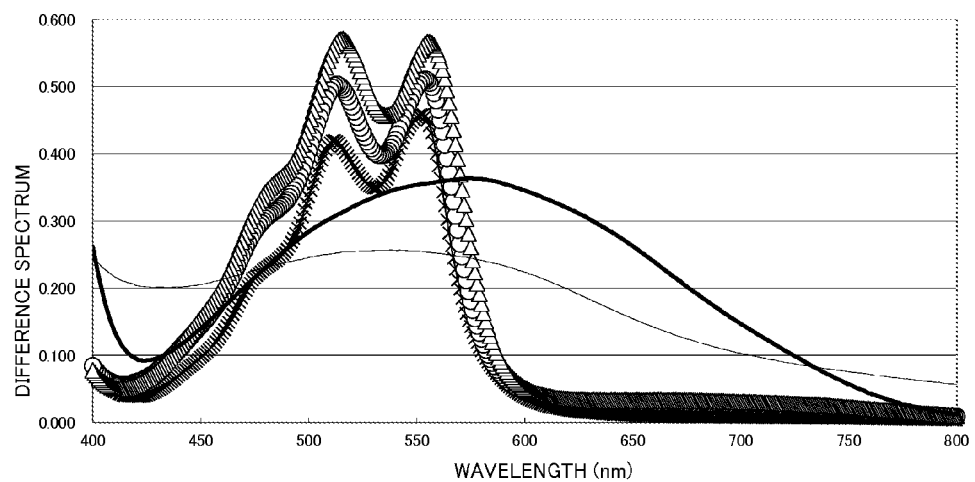
FIG. 1 is a figure illustrating an absorption spectrum which is measured in Example 1.

Hereinafter, the present invention will be described.

In the present invention, any numerical range expressed herein using "to" refers to a range including the numerical values before and after the "to", as a minimum value and a maximum value, respectively.

In a case in which the amount of a component in the composition is indicated in the present specification, when there are plural substances corresponding to the component in the composition, the indicated amount means the total amount of the plural substances present in the composition, unless specifically stated otherwise.

<Reagent for Measuring a Degree of Oxidative Stress>

The reagent for measuring a degree of oxidative stress of the present invention includes a compound represented by the following general formula (I) or a salt thereof. The compound represented by the general formula (I) or the salt thereof functions as a color forming dye. The compound represented by the following general formula (I) or the salt thereof can be used in manufacturing a reagent for measuring a degree of oxidative stress. Moreover, in the following description, there are cases when the compound represented by the general formula (I) or the salt thereof is, arbitrarily, collectively referred to as "a specific color forming dye".

The reagent for measuring a degree of oxidative stress of the present invention includes both the compound represented by the following general formula (I) or the salt thereof themselves, and a composition that contains at least the compound represented by the following general formula (I) or the salt thereof and a buffer solution.

The reagent for measuring a degree of oxidative stress of the present invention may be manufactured by a method of manufacturing that includes mixing the compound represented by the following general formula (I) or the salt thereof and a buffer solution.

The reagent for measuring a degree of oxidative stress of the present invention can be used in a method of measuring a degree of oxidative stress. Detailed description of the method of measuring a degree of oxidative stress to which the reagent for measuring a degree of oxidative stress of the present invention can be applied will be given later.

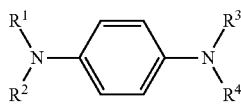
(I)

In the general formula (I), $R^1$, $R^2$, $R^3$ and $R^4$ each independently represent a hydrogen atom, an ethyl group, an isopropyl group, a hydroxyalkyl group having 1 to 4 carbon atoms (for example, a hydroxymethyl group, a hydroxyethyl group, a hydroxypropyl group are included, and 2-hydroxyethyl group is preferable.), or a phenyl group.

In the general formula (I), at least one of $R^1$, $R^2$, $R^3$ or $R^4$ represents an isopropyl group, a hydroxyalkyl group having 1 to 4 carbon atoms, or a phenyl group, and two or more of $R^1$, $R^2$, $R^3$ or $R^4$ each independently may represent an isopropyl group, a hydroxyalkyl group having 1 to 4 carbon atoms, or a phenyl group.

In a case where two or more of $R^1$, $R^2$, $R^3$ or $R^4$ each independently represent an isopropyl group, a hydroxyalkyl group having 1 to 4 carbon atoms, or a phenyl group, it may be the same groups of two or more, or it may be each independently different groups of two or more.

In one of the preferred aspects of a specific color forming dye, an aspect in which at least one of $R^1$, $R^2$, $R^3$ or $R^4$ is a hydroxyalkyl group having 1 to 4 carbon atoms (hereinafter, there are some cases where the specific color forming dye of this aspect is referred to as a "specific color forming dye A") is included. The specific color forming dye A in which at least one of $R^1$, $R^2$, $R^3$ or $R^4$ is a hydroxyalkyl group having 1 to 4 carbon atoms exhibits higher sensitivity and a sharp absorption, as compared to a conventional well-known compound that is used as a reagent for measuring a degree of oxidative stress. Therefore, it is possible to perform the measurement of the degree of oxidative stress with higher accuracy by selecting the specific color forming dye A.

In one of another preferred aspects of a specific color forming dye, an aspect in which at least one of $R^1$, $R^2$, $R^3$ or $R^4$ is a phenyl group (hereinafter, there are some cases where the specific color forming dye of this aspect is referred to as a "specific color forming dye B") is included. In a case where at least one of $R^1$, $R^2$, $R^3$ or $R^4$ is a phenyl group, the specific color forming dye B that undergo coloration has an absorption wavelength in a wide wavelength range of from 420 nm to 800 nm, although the absorption wavelength is different depending on a molecular structure of the specific color forming dye B.

Therefore, for example, in a case of using blood as a biological sample of measurement of the degree of oxidative stress, it is possible to measure the degree of oxidative stress with higher accuracy, by selecting the specific color forming dye B that also has an absorption wavelength in a wavelength range of the long-wavelength side (for example, a range of 600 nm or more) which is not affected by interference due to the existence of serum components such as protein.

In addition, there are some cases where a fluctuation of measuring sensitivity occurs according to the types of measurement devices. Even in those cases, the specific color forming dye B has an advantage in which it is hard to be affected by sensitivity fluctuation due to measurement devices since the specific color forming dye B has an absorption wavelength in a wide wavelength range. In particular, in a case of using an LED (light emitting diode) as a light source of measurement, there are some cases where measuring sensitivity fluctuates due to the difference between lots of LEDs. Even in this case, it is possible to measure of oxidative stress with higher sensitivity by using the specific color forming dye B.

In addition, the specific color forming dye may have an aspect that includes the characteristics of both specific color forming dye A and B. That is, the specific color forming dye may be an aspect in which at least one of $R^1$, $R^2$, $R^3$ or $R^4$ is a phenyl group, and at least one of $R^1$, $R^2$, $R^3$ or $R^4$ is a hydroxyalkyl group having 1 to 4 carbon atoms. In this case, in the compound represented by the general formula (I), a nitrogen atom to which a phenyl group is bonded and a nitrogen atom to which the hydroxyalkyl group having 1 to 4 carbon atoms is bonded may be the same as or different from each other.

In a case where the specific color forming dye is a compound which has a substituent in $R^1$, $R^2$, $R^3$ or $R^4$ described above other than a phenyl group as $R^1$, $R^2$, $R^3$ or $R^4$ in the general formula (I), the specific color forming dye may be the salt of the compound represented by the general formula (I).

In a case where the specific color forming dye is a salt of the compound represented by the general formula (I), examples of the salt includes a hydrochloride, a sulfate, an oxalate, or the like.

As the specific color forming dye in the present invention, a salt of the compound represented by the general formula (1)

is more preferable, from a viewpoint of solubility to a solvent when a sample solution is prepared.

As $R^1$, $R^2$, $R^3$ and $R^4$ in the general formula (I), an aspect in which $R^1$ is a hydrogen atom, $R^2$ is a hydrogen atom or an isopropyl group, $R^3$ is a hydrogen atom, an ethyl group, or a hydroxyalkyl group having 1 to 4 carbon atoms, and $R^4$ is a hydroxyalkyl group having 1 to 4 carbon atoms or a phenyl group is included. The specific color forming dye in the present invention is not limited thereto.

In addition, as another example of the specific color forming dye, in the general formula (I), hydrochloride, sulfate, and oxalate of a compound in which $R^1$ is a hydrogen atom, $R^2$ is a hydrogen atom, $R^3$ is an ethyl group, or a hydroxyalkyl group having 1 to 4 carbon atoms, and $R^4$ is a hydroxyalkyl group having 1 to 4 carbon atoms are included. The specific color forming dye in the present invention is not limited thereto.

Specific examples of the specific color forming dye are shown below, but the specific color forming dye in the present invention is not limited thereto.

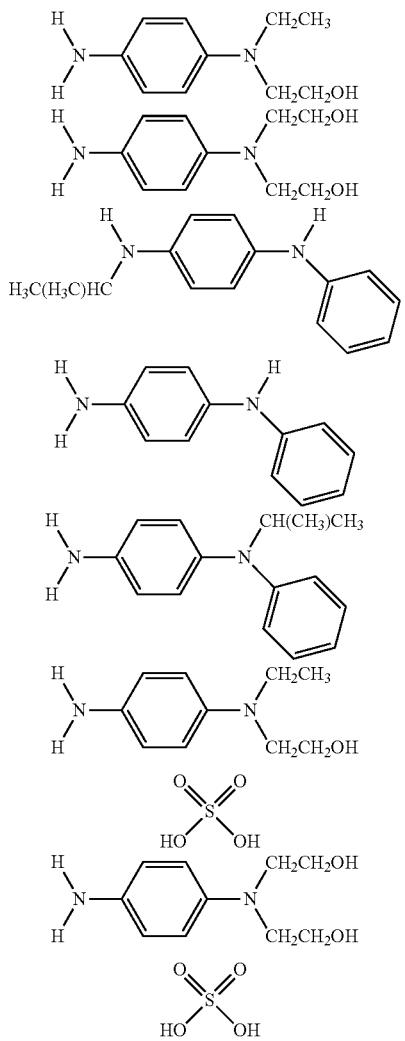

<A Method of Measuring a Degree of Oxidative Stress>

A method of measuring a degree of oxidative stress of the present invention (Hereinafter, arbitrarily, referred to as a "method of measurement of the present invention") is a method of measuring a degree of oxidative stress in a biological sample using the reagent for measuring a degree of oxidative stress which includes the compound represented by the general formula (I) described before or the salt thereof (the specific color forming dye). The method of measurement of the present invention is a method of comprehensively evaluating the degree of oxidative stress in vivo by measuring the concentration of hydroperoxide (R—OOH) in the biological sample by a coloring reaction.

In the method of measurement of the present invention, hydroperoxide (R—OOH) which is a target for measurement is a general term for a lipid, a protein, an amino acid, a nucleic acid, or the like which undergoes oxidation reaction by a reactive oxygen or free radicals, and is a marker of the degree of oxidative stress. The biological sample used in the method of measurement of the present invention includes blood, a product derived from blood such as blood plasma, urine, or the like.

The method of measurement of the present invention is preferably a method in which an absorbance of a sample solution that is colored by a first reaction and a second reaction described below is measured using a spectral photometer, and the concentration of hydroperoxide (R—OOH) is calculated from a measured value that is obtained.

The first reaction:

A reaction that includes obtaining the sample solution by mixing the biological sample in a buffer solution in which a transition metal salt and the specific color forming dye are dissolved and which is adjusted to the predetermined pH, and generating free radicals consisting of alkoxy radicals (R—OO) and hydroperoxyl radicals (R—OO) by decomposing hydroperoxide (R—OOH) that is included in the biological sample using a transition metal ion derived from the transition metal salt as a catalyst in the sample solution that is obtained.

The second reaction:

A reaction that makes the specific color forming dye contained in the sample solution generate color due to free radicals consisting of alkoxy radicals (R—O) and hydroperoxyl radicals (R—OO) generated in the sample solution in the first reaction.

As the buffer solution described above, for example, an acetate buffer solution, a phosphate buffer solution, a tris-maleate buffer solution, a citrate buffer solution, a 2-(N-morpholino) ethanesulfonic acid (MES) buffer solution, a N-(2-acetamido) iminodiacetic acid (ADA) buffer solution, a bis-tris buffer solution, and the like are included, an acetate buffer solution, a MES buffer solution, or a tris-maleate buffer solution is preferable, and an acetate buffer solution is more preferable.

As pH of the buffer solution described above, pH of from 3.6 to 5.6 is preferable, and pH of from 4.6 to 5.4 is more preferable. As a concentration of the buffer solution described above, from 100 mM to 400 mM is preferable, and from 200 mM to 400 mM is more preferable.

As the transition metal salt described above, for example, iron sulfate (II), copper sulfate (I), and the like are included, and iron sulfate (II) is preferable. As a concentration of the transition metal salt in the buffer solution described above, from 0.06 mM to 0.0005 mM is preferable, and from 0.03 mM to 0.001 mM is more preferable.

As a concentration of the specific color forming dye in the buffer solution described above, from 0.4 mM to 8 mM is preferable, and from 0.8 mM to 6.4 mM is more preferable.

The measurement is usually and preferably performed within a temperature range of from 20° C. to 40° C.

As a measurement device that can be applied to the method of measurement of the present invention, there is not limit as long as a measurement device is a device in which the method of measurement of the present invention is capable of performing. As such a measurement device, for example, a measurement device described in JP-A No. 2009-257909 may be used. In addition, as a measurement device, a commercial product in which the method of measurement of the present invention is capable of performing may be used.

EXAMPLES

Hereinafter, detailed description will be given of the present invention in Examples. However, the present invention is not limited thereto.

Example 1

Each compound shown in Table 1 was designated as a color forming dye, and sample solutions of the following formulation A were prepared for every color forming dye. The color forming dye was reacted with hydrogen peroxide in each sample solution that was prepared to make the color forming dye generate color.

Separately from each sample solution after coloring, sample solutions in which only the hydrogen peroxide is removed from the sample solutions of the following formulation, were respectively produced and designated as sample solutions before coloring.

For each sample solution after coloring and before coloring, absorption spectra were measured using a photometer (product name: Spectral Photometer V-550, manufactured by JASCO Corporation), the difference spectra thereof were determined, and these are shown in FIG. 1. In FIG. 1, a white triangle, a white circle, a thick line, a thin line and "x" show the results in cases where a color forming dye (1), a color forming dye (2), a color forming dye (3), a color forming dye (4) and a comparative color forming dye are respectively used.

—Formulation A—

| Acetate buffer solution (pH 5.0) | 300 mM |
|---|---|
| FeSO$_4$ | 0.03 mM |
| Color forming dye (each color forming dye shown in Table 1) | 3.2 mM |
| Hydrogen peroxide | 0.003% by mass |

In Table 1, the color forming dyes (1) to (4) used in Example 1 are the specific color forming dye according to the reagent for measuring a degree of oxidative stress of the present invention, the color forming dyes (1) and (2) are included in the specific color forming dye A, and the color forming dyes (3) and (4) are included in the specific color forming dye B. The comparative color forming dye is a conventional well-known color forming dye. The color forming dyes (1) and (2) are used as sulfate.

From the results shown in FIG. 1, the following is understood.

For the color forming dyes (1) and (2) which have a 2-hydroxyethyl group as a substituent, it is understood that the absorption wavelength is almost the same but sharper, and that sensitivity is notably higher, as compared to the comparative color forming dye.

It is understood that the color forming dyes (3) and (4) which have a phenyl group as a substituent have an absorption wavelength in a wider range, and that it is more possible to perform measurement at the long-wavelength side than heretofore, as compared to the comparative color forming dye.

From the above, it is understood that it is possible to measure a degree of oxidative stress with high accuracy by using the reagent for measuring a degree of oxidative stress which includes the specific color forming dye according to the present invention.

Example 2

Each compound shown in Table 1 was designated as a color forming dye, and sample solutions of the following formulation B were prepared for every color forming dye. The color forming dye was reacted with t-butyl peroxide (t-BuOOH) in each sample solution that was prepared to make the color forming dye generate color.

For each sample solution after coloring, the following comparative tests A or B were performed to compare reactivity of each color forming dye.

—Comparative Test A—

For each sample solution after coloring that includes the color forming dye (1), the color forming dye (2), or the comparative color forming dye, absorption spectra were measured at the wavelength of 510 nm using a photometer (product name: Spectral Photometer V-550, manufactured by JASCO Corporation) to compare reactivity of each color

TABLE 1

R$^1$R$^2$N—C$_6$H$_4$—NR$^3$R$^4$

Figure 2:
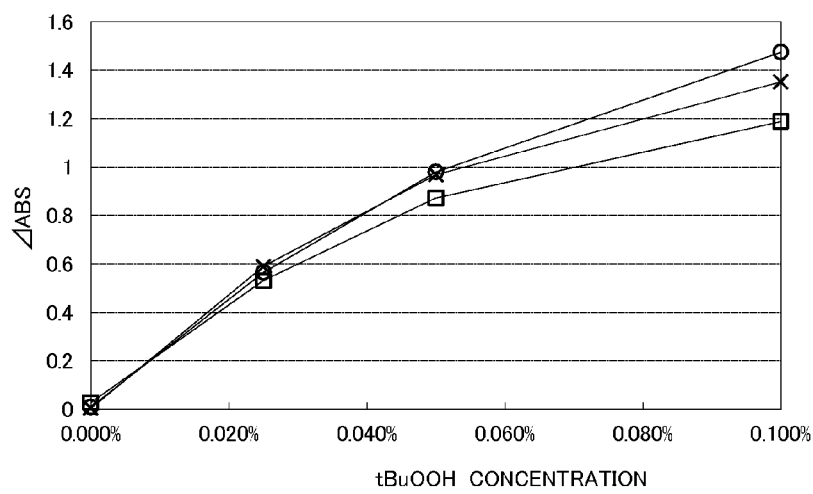
FIG. 2 is a figure illustrating the result of test A which is performed in Example 2.

| | R$^1$ | R$^2$ | R$^3$ | R$^4$ |
|---|---|---|---|---|
| Comparative color forming dye | —H | —H | —CH$_2$CH$_3$ | —CH$_2$CH$_3$ |
| Color forming dye (1) | —H | —H | —CH$_2$CH$_3$ | —CH$_2$CH$_2$OH |
| Color forming dye (2) | —H | —H | —CH$_2$CH$_2$OH | —CH$_2$CH$_2$OH |
| Color forming dye (3) | —H | —CH(CH$_3$)CH$_3$ | —H | 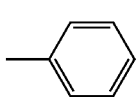 |
| Color forming dye (4) | —H | —H | —H | 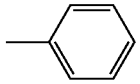 | forming dye. The result of the coloring test A is shown in FIG. 2. In FIG. 2, "x" shows the result in a case of using the color forming dye (1), a "white circle" shows the result in a case of using the color forming dye (2), and a "white square" shows the result in a case of using the comparative color forming dye.

—Comparative Test B—

Figure 3:
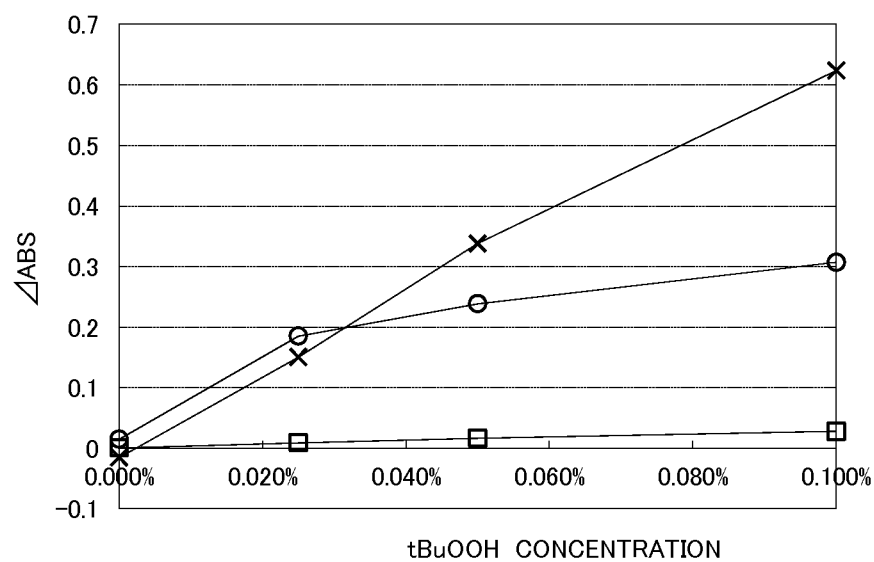
FIG. 3 is a figure illustrating the result of test B which is performed in Example 2.

For each sample solution after coloring that includes the color forming dye (3), the color forming dye (4), or the comparative color forming dye, absorption spectra were measured at the wavelength of 660 nm using a photometer (product name: Spectral Photometer V-550, manufactured by JASCO Corporation) to compare reactivity of each color forming dye. The result of the coloring test B is shown in FIG. 3. In FIG. 3, "x" shows the result in a case of using the color forming dye (3), a "white circle" shows the result in a case of using the color forming dye (4), and a "white square" shows the result in a case of using the comparative color forming dye.

—Formulation B—

| Acetate buffer solution (pH 5.0) | 300 mM |
|---|---|
| FeSO$_4$ | 0.03 mM |
| Color forming dye (each color forming dye shown in Table 1) | 3.2 mM |
| t-BuOOH | Prepared to each concentration of measurement (% by mass) shown in FIG. 2 or FIG. 3 |

From the results shown in FIG. 2 and FIG. 3, the following is understood.

As shown in FIG. 2, it is understood that the color forming dyes (1) and (2) which have a 2-hydroxyethyl group as a substituent have higher sensitivity in any of t-BuOOH concentrations, as compared to the comparative color forming dye, in a case of comparing at the peak wavelength (510 nm).

As shown in FIG. 3, it is understood that the color forming dyes (3) and (4) which have a phenyl group as a substituent have notably higher reactivity even at the wavelength of 660 nm, as compared to the comparative color forming dye, and that it is possible to perform measurement of the degree of oxidative stress in a wavelength range at the long-wavelength side, in which measurement was conventionally difficult.

As described above, it has become clear that, according to the present invention, a reagent for measuring a degree of oxidative stress which is capable of measuring a degree of oxidative stress with higher sensitivity or in a wider wavelength range than heretofore, and a method of measuring a degree of oxidative stress using the reagent for measuring a degree of oxidative stress can be provided.

The invention claimed is:

1. A reagent for measuring a degree of oxidative stress, comprising a compound represented by the following general formula (I) or a salt thereof:

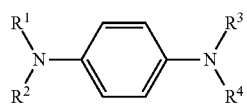

(I)

wherein, in the general formula (I),
$R^1$ is a hydrogen atom; $R^2$ is an isopropyl group; $R^3$ is a hydrogen atom, an ethyl group, or a hydroxyalkyl group having 1 to 4 carbon atoms; and $R^4$ is a hydroxyalkyl group having 1 to 4 carbon atoms or a phenyl group;

$R^1$ is a hydrogen atom; $R^2$ is a hydrogen atom; $R^3$ is a hydrogen atom; and $R^4$ is a hydroxyalkyl group having 1 to 4 carbon atoms or a phenyl group;

$R^1$, $R^2$, $R^3$ and $R^4$ each independently is an ethyl group, an isopropyl group, a hydroxyalkyl group having 1 to 4 carbon atoms, or a phenyl group, where at least one $R^1$, $R^2$, $R^3$ or $R^4$ is an isopropyl group, a hydroxyalkyl group having 1 to 4 carbon atoms, or a phenyl group; or at least one of $R^1$, $R^2$, $R^3$ or $R^4$ is a phenyl group, and at least one of $R^1$, $R^2$, $R^3$ or $R^4$ is a hydroxyalkyl group having 1 to 4 carbon atoms, and a nitrogen atom to which the phenyl group is bonded and a nitrogen atom to which the hydroxyalkyl group having 1 to 4 carbon atoms is bonded are different from each other.

2. A reagent according to claim 1, wherein at least one of $R^1$, $R^2$, $R^3$ or $R^4$ is a hydroxyalkyl group having 1 to 4 carbon atoms.

3. A reagent according to claim 1, wherein at least one of $R^1$, $R^2$, $R^3$ or $R^4$ is a 2-hydroxyethyl group.

4. A reagent according to claim 1, wherein at least one of $R^1$, $R^2$, $R^3$ or $R^4$ is a phenyl group.

5. A reagent according to claim 1, wherein two or more of $R^1$, $R^2$, $R^3$ or $R^4$ each independently is an isopropyl group, a hydroxyalkyl group having 1 to 4 carbon atoms, or a phenyl group.

6. A reagent according to claim 1, wherein at least one of $R^1$, $R^2$, $R^3$ or $R^4$ is a phenyl group and at least one of $R^1$, $R^2$, $R^3$ or $R^4$ is a hydroxyalkyl group having 1 to 4 carbon atoms.

7. A reagent according to claim 1, comprising a salt of the compound represented by the general formula (I) selected from the group consisting of a hydrochloride, a sulfate, and an oxalate.

8. A reagent according to claim 1, wherein the compound represented by the general formula (I) is selected from the group consisting of:

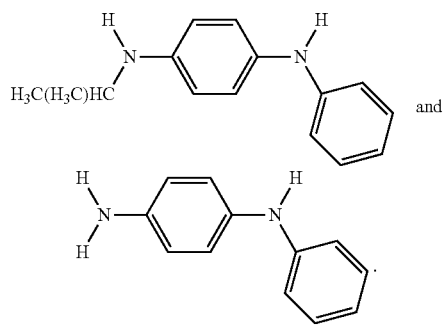

and

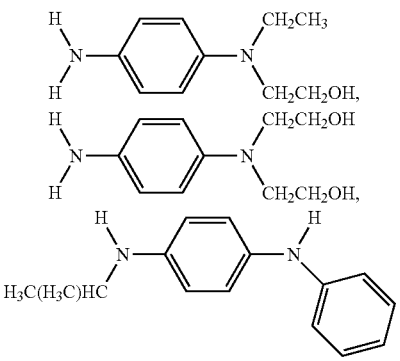

,

-continued

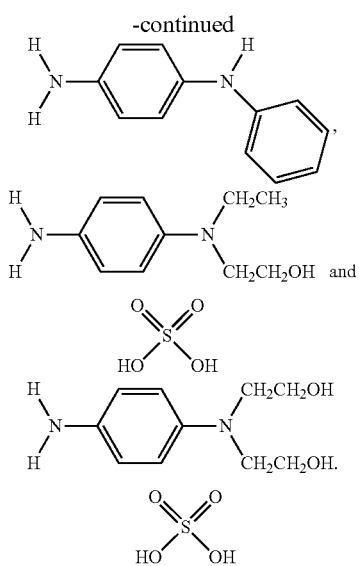

9. A reagent comprising a compound represented by the general formula (I) or a salt thereof as defined in claim 1, and a buffer.

10. A reagent according to claim 9, wherein the buffer is selected from the group consisting of an acetate buffer solution, a phosphate buffer solution, a tris-maleate buffer solution, a citrate buffer solution, a 2-(N-morpholino) ethanesulfonic acid (MES) buffer solution, a N-(2-acetamido) iminodiacetic acid (ADA) buffer solution and a bis-tris buffer solution.

11. A method of determining the concentration of hydroperoxide in a biological sample, the method comprising:
(a) mixing the biological sample with a buffer solution which comprises a transition metal salt and a color forming dye, wherein the color forming dye comprises a compound represented by the following general formula (I) or a salt thereof;

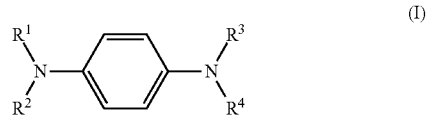

(b) measuring absorbance of the resulting sample solution with a spectral photometer; and
(c) determining concentration of the hydroperoxide from the measured value that is obtained,
wherein, in the general formula (I),
$R^1$, $R^2$, $R^3$ and $R^4$ each independently is a hydrogen atom, an ethyl group, an isopropyl group, a hydroxyalkyl group having 1 to 4 carbon atoms, or a phenyl group, where at least one of $R^1$, $R^2$, $R^3$ or $R^4$ is an isopropyl group, a hydroxyalkyl group having 1 to 4 carbon atoms, or a phenyl group.

12. A method according to claim 11, wherein the biological sample is blood, a product derived from blood, or urine.

* * * * *